United States Patent
Prasad et al.

[11] Patent Number: 6,075,157
[45] Date of Patent: Jun. 13, 2000

[54] PURIFICATION OF O,S-DIMETHYL PHOSPHORAMIDOTHIOATE

[75] Inventors: Vidyanatha A. Prasad, Leawood; Klaus Jelich, Overland Park, both of Kans.

[73] Assignee: Bayer Corporation, Pittsburgh, Pa.

[21] Appl. No.: 09/134,971

[22] Filed: Aug. 17, 1998

[51] Int. Cl.[7] .......................................................... C07F 9/24
[52] U.S. Cl. ............................................. 558/88; 558/146
[58] Field of Search ....................................... 558/146, 88

[56] References Cited

U.S. PATENT DOCUMENTS 3,309,266  3/1967  Magee .
3,639,547  2/1972  Magee .
4,389,350  6/1983  Lonsinger et al. .

*Primary Examiner*—Michael G. Ambrose
*Attorney, Agent, or Firm*—Joseph C. Gil; Carol Marmo

[57] ABSTRACT

The present invention provides a method for making O,S-dimethyl phosphoramidothioate. In accordance with this process, O,O-dimethyl phosphoramidothioate is isomerized in the presence of dimethyl sulfate to form a reaction mixture; the reaction mixture is then passed through a wiped film evaporator at a temperature of from about 55° C. to about 120° C. and a pressure of from about 3 to about 10 mm Hg, with the distillate containing O,S-dimethyl phosphoramidothioate, unreacted O,O-dimethyl phosphoramidothioate and by-products, and the residue containing O,S-dimethyl phosphoramidothioate in an amount greater than the amount of O,S-dimethyl phosphoramidothioate contained in the reaction mixture prior to distillation.

8 Claims, No Drawings

PURIFICATION OF O,S-DIMETHYL PHOSPHORAMIDOTHIOATE

The field of this invention is phosphoramidothioate insecticides. More particularly, the present invention pertains to an improved, commercially-viable process for the purification of O,S-dimethyl phosphoramidothioate.

BACKGROUND OF THE INVENTION

O,S-dialkyl phosphoramidothioates are effective insecticides. One particularly effective insecticide is O,S-dimethyl phosphoramidothioate (See, e.g., U.S. Pat. Nos. 3,309,266; 3,639,547; 3,309,266; and 4,389,350; the disclosures of which are incorporated herein by reference). U.S. Pat. No. 3,309,266 discloses that O,S-dimethyl phosphoramidothioate can be made by reacting O,O-dimethyl chlorophosphorothioate with ammonia or a primary alkylamine and then heating the product of that reaction in the presence of an alkylating reagent such as an alkyl halide. U.S. Pat. No. 3,639,547 discloses that O,S-dimethyl phosphoramidothioate can be made by reacting O,O-dimethyl phosphoramidothioate with the dimethyl ester of sulfuric acid or with a methyl ester of organic sulfonic acids. The reaction occurs at a temperature of from about 20° C. to about 100° C. In a manner similar to the method disclosed in U.S. Pat. No. 3,309,266, the O,O-dimethyl phosphoramidothioate can be made via ammoniation of a O,O-dimethyl halophosphorothioate. U.S. Pat. No. 4,389,350 discloses a catalytic isomerization of O,O-dimethyl phosphoramidothioate to O,S-dimethyl phosphoramidothioate wherein the reaction mixture is separated into "starting material" and isomerized product, to effect further isomerization of the "starting material".

With the above methods, the yield and purity of the formed O,S-dimethyl phosphoramidothioate are low, ranging from about 30% to about 70%, or the purification process is extensive requiring repeated isomerization steps. There continues to be a need in the art, therefore for an efficient method for making O,S-dimethyl phosphoramidothioate at an increased yield and purity.

BRIEF SUMMARY OF THE INVENTION

The present invention provides a method for increasing the yield and purity of O,S-dimethyl phosphoramidothioate. In accordance with the present process:

(1) O,O-dimethyl phosphoramidothioate is isomerized in the presence of dimethyl sulfate to form a reaction mixture containing from about 70% to about 85% by weight of O,S-dimethyl phosphoramidothioate, and the balance being unreacted O,O-dimethyl phosphoramidothioate and by-products;

(2) the reaction mixture is then passed through a wiped film evaporator; and (3) the distillate contains O,S-dimethyl phosphoramidothioate, unreacted O,O-dimethyl phosphoramidothioate and by-products; with the residue containing O,S-dimethyl phosphoramidothioate in an amount greater than the amount of O,S-dimethyl phosphoramidothioate contained in the reaction mixture of the first step.

It is an object of this invention to provide an improved process for purifying O,S-dimethyl phosphoramidothioate. It is a further object of this invention to reduce the level of O,O-dimethyl phosphoramidothioate in the resultant product.

DETAILED DESCRIPTION OF THE INVENTION

The present invention provides a method for increasing the yield and purity of O,S-dimethyl phosphoramidothioate. O,O-dimethyl phosphoramidothioate is isomerized in the presence of dimethyl sulfate at a temperature of from about 20° C. to about 80° C., and preferably at a temperature of from about 35° C. to about 45° C. Dimethyl sulfate is present in an amount of from about 3% to about 5% by weight of the amount of O,O-dimethyl phosphoramidothioate utilized in the reaction mixture; and preferably from about 4% to about 4.5% by weight. The time needed for the isomerization reaction depends on the reaction temperature and can vary from about 8 hours at the lower temperatures to about 45 minutes at the higher temperatures. Preferably, the reaction time is about 6 hours (at 40° C.). The resultant mixture contains from about 70% to about 85% by weight of O,S-dimethyl phosphoramidothioate, and preferably 75% to about 80% by weight of O,S-dimethyl phosphoramidothioate; the balance being unreacted O,O-dimethyl phosphoramidothioate and by-products. The reaction mixture is then passed through a wiped film evaporator, to strip-off the lower boiling O,O-dimethyl phosphoramidothioate, at a temperature of from about 55° C. to about 120° C., and preferably at a temperature of from about 85° C. to about 115° C.; and a pressure of from about 3 mm Hg to about 10 mm Hg, and preferably from a pressure of about 5 mm Hg to about 8 mm Hg. The resultant distillate contains O,S-dimethyl phosphoramidothioate, unreacted O,O-dimethyl phosphoramidothioate and by-products; the residue containing O,S-dimethyl phosphoramidothioate in an amount greater than the amount of O,S-dimethyl phosphoramidothioate in the isomeric mixture, prior to being passed through the evaporator.

O,O-dimethyl phosphoramidothioate is used in the reaction to produce O,S-dimethyl phosphoramidothioate and can be prepared using any process well known in the art. In one embodiment, O,O-dimethyl phosphoramidothioate is made via ammoniation of a O,O-dimethylhalophosphorothioate such as O,O-dimethylchloro-phosphorothioate (DMPCT). Typically, the DMPCT in an aromatic solvent such as toluene, benzene or xylene is reacted with ammonia. The solvent is removed prior to the methylation-isomerization step set forth above.

The Examples that follow illustrate preferred embodiments of the present invention and are not limiting of the specification and claims in any way.

EXAMPLES

Example 1
Preparation of O,S-Dimethyl Phosphoramidothioate

About 500 grams of O,O-dimethyl phosphoramidothioate and about 21.25 grams of dimethyl sulfate were passed through an isomerizer. The reaction mixture was heated to a temperature of about 69° C. and maintained at that temperature for about 1.5 hours. The resultant mixture contained 77% active ingredient. The mixture was then passed through a wiped film evaporator at various temperatures between 25° C. and105° C. (see Table 1 below), and a pressure of about 5.25 mm Hg. The results are shown in Table 1.

TABLE 1

| Temperature (° C.) | Isomeric Mixture (% A. I.) |
| --- | --- |
| 25 | 77.0 |
| 85 | 79.0 |
| 90 | 80.0 |
| 95 | 80.6 |

TABLE 1-continued

| Temperature (° C.) | Isomeric Mixture (% A. I.) |
|---|---|
| 100 | 80.7 |
| 105 | 81.1 |

Example 2
Preparation of O,S-Dimethyl Phosphoramidothioate

About 500 grams of O,O-dimethyl phosphoramidothioate and about 21.25 grams of dimethyl sulfate were passed through an isomerizer. The reaction mixture was heated to a temperature of about 40° C. and maintained at that temperature for about 6 hours. The resultant mixture contained 81% active ingredient. The mixture was then passed through a wiped film evaporator at various temperatures between 25° C. and 115° C. (see Table 2 below), and a pressure of about 5.25 mm Hg. The results are shown in Table 2.

TABLE 2

| Temperature (° C.) | Isomeric Mixture (% A. I.) |
|---|---|
| 25 | 81.0 |
| 85 | 82.9 |
| 90 | 83.3 |
| 100 | 83.7 |
| 110 | 84.4 |
| 115 | 84.4 |

Tables 1 and 2 demonstrate that the purity of O,S-dimethyl phosphoramidothioate can be increased by stripping off the lower boiling O,O-dimethyl phosphoramidothioate. The distillate constituted two parts O,O-dimethyl phosphoramidothioate to one part O,S-dimethyl phosphoramidothioate and 30% lower boiling by-products. The distillate may then be recycled for use in the next isomerization batch.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing O,S-dimethyl phosphoramidothioate comprising:

a. isomerizing O,O-dimethyl phosphoramidothioate in the presence of dimethyl sulfate at a temperature of from about 20° C. to about 80° C., to form a reaction mixture containing from about 70% to about 85% by weight of O,S-dimethyl phosphoramidothioate, and the balance being unreacted O,O-dimethyl phosphoramidothioate and by-products; and b. passing said reaction mixture through a wiped film evaporator at a temperature of from about 55° C. to about 120° C. and a pressure of from about 3 to about 10 mm Hg, with the distillate containing O,S-dimethyl phosphoramidothioate, unreacted O,O-dimethyl phosphoramidothioate and by-products, and the residue containing O,S-dimethyl phosphoramidothioate in an amount greater than the amount of O,S-dimethyl phosphoramidothioate contained in said reaction mixture of step a).

2. The process of claim 1 wherein the reaction temperature in step a.) is from about 35° C. to about 45° C.

3. The process of claim 1 wherein the reaction mixture of step a.) contains from about 75% to about 80% by weight of O,S-dimethyl phosphoramidothioate.

4. The process of claim 1 where in the evaporator temperature in step b.) is from about 85° C. to about 115° C.

5. The process of claim 1 wherein the pressure is from about 5 mm Hg to about 8 mm Hg.

6. The process of claim 1 wherein the concentration of dimethyl sulfate is from about 3% to about 5% by weight of the O,O-dimethyl phosphoramidothioate utilized in the reaction mixture.

7. The process of claim 1 wherein the concentration of dimethyl sulfate is from about 4% to about 4.5% by weight of the O,O-dimethyl phosphoramidothioate utilized in the reaction mixture.

8. The process of claim 1 wherein the distillate of step b) is recycled for use in step a).

* * * * *